US004001731B2

United States Statutory Invention Registration [19]

[11] Reg. Number: H1731

[45] Published: Jun. 2, 1998

Ahr

[54] INSECT REPELLENT ARTICLE

[76] Inventor: Nicholas Albert Ahr, The Procter & Gamble Company, Winton Hill Technical Center, 6100 Center Hill Ave., Cincinnati, Ohio 45224

[21] Appl. No.: 539,284

[22] Filed: Oct. 4, 1995

[51] Int. Cl.[6] ..... A01N 25/00

[52] U.S. Cl. ..... 424/405

[58] Field of Search ..... 428/137, 131, 428/905; 43/125, 131; 424/403, 411, 443, DIG. 10, DIG. 7; 239/36, 43, 44, 45, 53, 54, 55, 56, 57, 58, 59

[56] References Cited

U.S. PATENT DOCUMENTS

| | | | |
|---|---|---|---|
| 4,094,119 | 6/1978 | Sullivan | 53/4 |
| 4,762,275 | 8/1988 | Herbert et al. | 239/6 |
| 5,242,111 | 9/1993 | Nakoneczny et al. | 239/47 |

FOREIGN PATENT DOCUMENTS

| | | | |
|---|---|---|---|
| 001041075 | 5/1953 | France | 20/3 |
| 94/10842 | 5/1994 | WIPO | A01N 25/28 |
| 94/27646 | 12/1994 | WIPO | A61L 9/12 |

*Primary Examiner*—Charles T. Jordan
*Assistant Examiner*—Meena Chelliah

[57] ABSTRACT

The present invention provides a portable, disposable article for repelling insects. The article includes a fibrous substrate which can be impregnated with the insect repellent. In one embodiment, the fibrous substrate is disposed intermediate a porous cover and a barrier layer, and comprises fibers having external capillary channels. The porous cover can comprise an apertured plastic film having tapered apertures. The insect repellent can be contained in a breakable packet, such that when the breakable packet is broken, the insect repellent is directed through the fibrous substrate for release through the apertured film.

1 Claim, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INSECT REPELLENT ARTICLE

FIELD OF THE INVENTION

This invention is related to an article for providing release of a volatile substance, and more particularly, to a portable, disposable article for providing release of an insect repellent.

BACKGROUND OF THE INVENTION

Bug or insect repellent for personal use has been historically delivered in a number of different ways. For example, it may be sprayed or wiped onto one's skin, sprayed into one's immediate environment, and/or sprayed onto one's clothing. The bug repellent solution is typically volatile so that vapors are emitted which repel bugs away from one's body.

Absorbent substrates saturated with volatile solutions of bug repellent, made in the form of patches, have been available for application to clothing. Typically, a patch containing a volatile solution must be contained in a package which prevents vaporization of the solution prior to application of the patch. U.S. patent application Ser. No. 08/369,068, "Package for Containing and Applying a Bug Repellent Patch" filed Jan. 5, 1995 in the name of Cook et al, discloses a package for containing a bug repellent impregnated patch. The disclosed package enables a user to apply the patch to a target surface without contacting the patch.

Such patches can have a barrier material between the substrate and a taget surface, such as a user's clothing. The barrier material can permit greater volumes of the volatile solution to be used to provide longer lasting protection from insects. As the amount of solution is increased, however, it is more likely that some of the solution may leak out of the substrate in liquid form, and possibly be absorbed into the user's skin, or be transferred from a finger into one's eye or mouth. Accordingly, the amount of solution that can be released in vapor form in a given amount of time, from a given surface area of the article, and for a given amount of liquid initially provided on the article is limited by the need to prevent contact of the volatile solution with the user's skin.

Accordingly, it is an object of the present invention to provide a portable, disposable article for providing release of a volatile substance, such as liquid insect repellent.

It is another object of the present invention to provide an article having a barrier layer, a porous cover layer, and a substrate impregnated with a volatile liquid bug repellent, wherein at least a portion of the substrate is disposed intermediate the barrier layer and the porous cover layer.

SUMMARY OF THE INVENTION

The present invention comprises a disposable, portable article for providing a controlled release of volatile material, such as an insect repellent, from a substrate.

The article provides a release of at least about 0.015 grams of the volatile material per hour, per square inch of the macroscopic surface area of the substrate impregnated with the volatile material, per gram of the volatile material initially impregnating the substrate. More preferably, the release rate is at least about 0.020 grams/gram-square inch-hour. In one embodiment, the release rate can be at least about 0.05 grams/gram-square inch-hour, more preferably at least about 0.1 grams/gram-square inch-hour, even more preferably at least about 0.15, and most preferably at least about 0.20 grams/gram-square inch-hour. In one embodiment, the article can provide a one hour release rate of at least about 0.02 grams/gram-square inch-hour, and a four hour release rate which is at least about 50 percent of the one hour release rate, and more preferably at least about 75 percent of the one hour release rate.

In one embodiment of the present invention, the article comprises a barrier layer and a porous cover layer, and a substrate impregnated with a volatile liquid material. The article can also comprise an adhesive fastener for attaching the article to a target surface, such as a wearer's garment. The porous cover layer can comprise an apertured plastic film having an open area ratio of at least about 10 percent, and more preferably at least about 20 percent.

The substrate can be impregnated with a volatile liquid material comprising an insect repellent. In one embodiment, the article can include a breakable vessel supported on the article. The vessel contains the volatile liquid substance, and is breakable by a user to direct the volatile liquid substance to the substrate. Accordingly, the volatile liquid substance is less likely to evaporate from the article prior to the time when the article is to be used.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Figure 1:
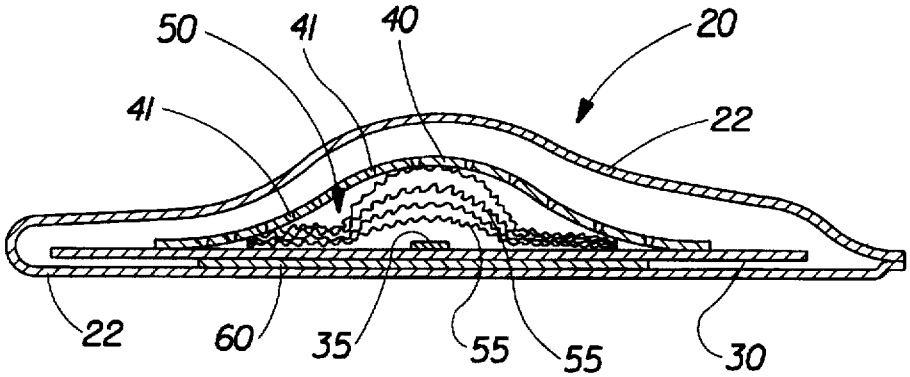
FIG. 1 is a cross-sectional view of an embodiment of the present invention wherein the article is enclosed in a sealed package.
Figure 2:
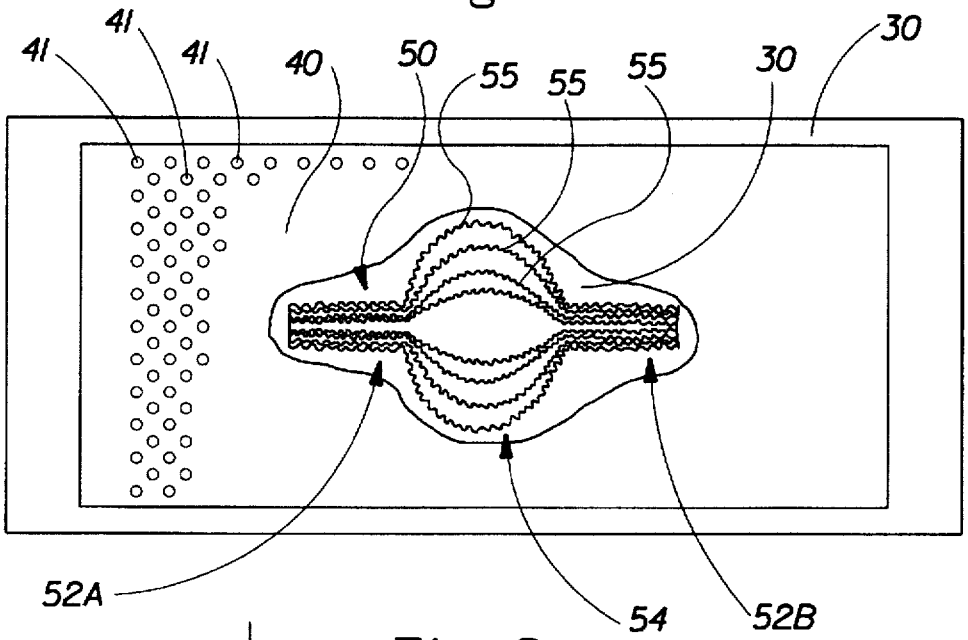
FIG. 2 is a top plan view of the article of FIG. 1, with the sealed package removed and the porous cover layer partially cut away to show a substrate having a relatively lower density region extending between relatively higher density regions.

FIGS. 1 and 2 show one embodiment of a disposable, portable article 20 according to the present invention for providing a release of volatile material comprising one or more components. In one embodiment, the article 20 comprises a substrate impregnated with a volatile liquid material, and the material released comprises an insect repellent. By the term "disposable" it is meant that the article 20 is intended to be discarded after a single use. By the term "portable" it is meant that the article 20 can be conveniently and comfortably carried in a pocket, purse, or handbag. By the term "volatile liquid material" it is meant a liquid material comprising a component having a vapor pressure of at least about 0.001 mm Hg at 50 degrees Centigrade.

In the embodiment shown in FIGS. 1–2, the article 20 comprises a barrier layer 30, a porous cover layer 40, and a substrate 50 impregnated with a volatile liquid material. The material with which the substrate 50 is impregnated preferably comprises a material effective for repelling insects.

The article 20 can also include a fastener 60, such as a pressure sensitive adhesive. The fastener 60 can be used to support the article 20 on a target surface, such as a wearer's garment. The article 20 can be sealed in wrapper 22 to prevent evaporation of the insect repellent prior to use of the article 20. In FIG. 2 the wrapper 22 is omitted to show the internal construction of the article 20.

Referring to the components of the article 20 in more detail, the barrier layer 30 is generally impervious to the volatile liquid substance. The barrier layer 30 prevents the volatile liquid substance in the substrate 50 from contacting the target surface on which article 20 is supported. In one embodiment the barrier layer 30 comprises a flexible film, such as a polymeric film; a flexible foil; or a composite material such as a foil/polymeric film laminate. By flexible it is meant that barrier 30 is compliant and readily conforms to the shapes and contours of the human body.

A suitable barrier layer 30 can comprise a woven or nonwoven material or a polymeric film such as thermoplastic film of polyethylene or polypropylene. A suitable thermoplastic film is a polyethylene film having a thickness of between about 0.012 mm to about 0.051 mm. Suitable films are manufactured by Clopay Corporation of Cincinnati, Ohio under the designation P18-0401 and by Ethyl Corp. of Terre Haute, Ind. under the designation XP-39385. Alternatively, the barrier layer 30 can comprise a laminate of foil and polymeric film, such as a Type M2077 foil/film laminate manufactured by the American Can Co. of Minn., Minn.

The fastener 60 can be joined directly or indirectly to the barrier layer 30, as shown in FIG. 1. Suitable fasteners 60 include, but are not limited to, adhesive fasteners and mechanical fasteners, such as VELCRO brand fasteners. Suitable pressure sensitive adhesives from which the fastener 60 can be formed are Century A-305-IV brand Adhesive manufactured by Century Adhesives Corp. of Columbus, Ohio; and Instant Lock 34-2823 brand adhesive manufactured by the National Starch and Chemical Company of Bridgewater, N.J.

The wrapper 22 can comprise a thermoplastic film incorporating a release liner for covering the fastener 60 while the article 20 is sealed in the wrapper 22. Suitable release liners for adhesive fasteners are described in U.S. Pat. No. 4,917,697, which patent is incorporated herein by reference. Non-limiting examples of suitable release liners are BL30MG-A Silox E1/0 and BL30MG-A Silox 4P/0 manufactured by the Akrosil Corp. of Menasha, Wis.

The porous cover layer 40 provides a release of an effective amount of the volatile substance from the article 20. The porous cover layer preferably provides a release rate of at least about 0.0150 grams of the volatile substance per square inch of the projected area of the impregnated substrate 50, per hour, per gram of the volatile substance initially impregnating the substrate. More preferably, the article 20 has a release rate of at least about 0.020 grams/gram-square inch-hour, even more preferably at least about 0.050 grams/gram-square inch-hour, still more preferably at least about 0.1 grams/gram-square inch-hour, and most preferably at least about 0.20 grams/gram-square inch-hour. The method for measuring release rates of the volatile substance from the article 20 is described below.

The porous cover layer 40 can comprise a film formed of a liquid impermeable material. A plurality of apertures 41 extend through the film. In one preferred embodiment, the porous cover layer can comprise an apertured formed plastic film having an outwardly facing surface 44, an inwardly facing surface 42. In one embodiment, apertured formed plastic films are preferred because they are generally non-absorbent with respect to the volatile liquid substance and help prevent the volatile liquid material from passing through the cover layer 40 to contact the wearer's skin or clothing.

The porous cover layer 40 can be joined to the barrier layer 30, either directly or indirectly, by a number of suitable methods. In the embodiment shown in FIG. 1, the perimeter of the cover layer 40 can be secured directly to the barrier layer 30 by adhesives, heat and/or pressure sealing, ultrasonic bonding, and the like. A suitable heat sealing method is disclosed in U.S. Pat. No. 5,382,245 issued Jan. 17, 1995 to Thompson et al.

In one embodiment, the porous cover layer has a caliper 45 of at least about 0.005 inch. The caliper 45 is measured under a compressive load of 95 grams per square inch using a circular load foot having a 2.00 inch diameter. The caliper 45 provides separation of the liquid in the substrate 50 from the outwardly facing surface 44 of the porous cover layer 40. Such a caliper 45 helps to restrict the liquid in the substrate 50 from reaching the surface 44, and possibly contacting the wearer's skin or clothing. In one embodiment, the caliper 45 can be at least about 0.010 inch, and more preferably at least about 0.015 inch. For example, a suitable porous cover layer 40 can have a caliper 45 between about 0.015 inch and about 0.025 inch.

Figure 3:
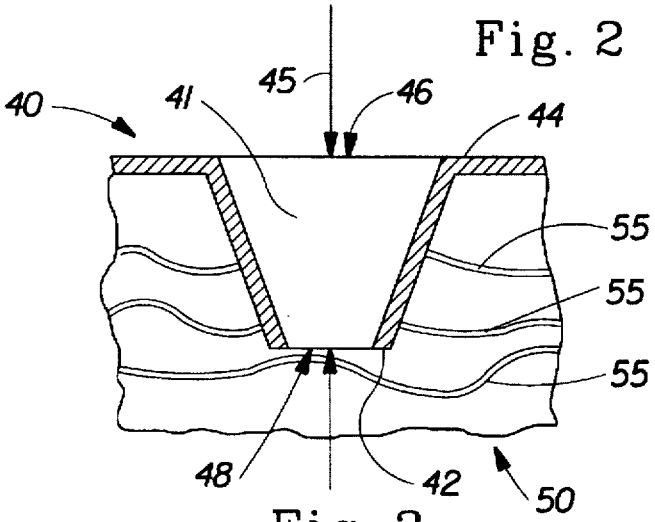
FIG. 3 is a enlarged cross-sectional view of a portion of the article of FIG. 1 showing a porous cover layer having generally conically shaped apertures.

The apertures 41 can also be shaped to restrict flow of the liquid from the substrate 50 to the outer surface 44. As shown in FIG. 3, the apertures 41 can be tapered from a relatively large base opening 46 at the outwardly facing surface 44 to a relatively smaller apex opening 48 at the inwardly facing surface 42. U.S. Pat. No. 3,929,135 issued Dec. 30, 1975 to Thompson is incorporated herein by reference for the purpose of disclosing a suitable formed film having tapered openings. In an alternative embodiment not shown, the apertures 41 can be tapered from a relatively large opening at the inward surface 42 to a relatively smaller apex at the outward surface 44.

Each of the openings 46 can each have a surface area between about 0.015 square mm and about 32 square mm. The porous cover layer 40 can have an open area ratio of at least about 10 percent. In one embodiment, the porous cover layer 40 has an open area ratio of at least about 20 percent. For instance, a suitable porous cover layer 40 can have an open area ratio between about 20 percent and about 50 percent. Such an open area ratio is suitable for providing effective release of the volatile material from the substrate.

The open area ratio is determined by first measuring the total surface area of the porous cover layer 40, as viewed in FIG. 2, including the area of the openings 46. The surface areas of all the openings 46 in the cover layer 40 are then measured and added. The surface areas of the openings 46 are measured at the outward surface 44. The open area ratio is the ratio of the sum of the areas of these openings 46 divided by the total surface area of the cover layer 40.

While the porous cover layer 40 is shown having tapered apertures 41 in FIGS. 1–3, it will be understood that other formed films can also be used to provide release of the volatile material from the article 20, while restricting flow of the liquid volatile material from the substrate 50 to the surface 44. Other formed films suitable for use as the cover layer 40 are disclosed in the following U.S. Patents, which are incorporated by reference herein: U.S. Pat. No. 4,324,246 issued to Mullane et al; U.S. Pat. No. 4,342,314 issued to Radel et al.; U.S. Pat. No. 4,463,045 issued to Ahr et al.; U.S. Pat. No. 4,629,643 issued to Curro et al.; and U.S. Pat. No. 5,006,394 issued to Baird. One suitable porous cover layer 40 is marketed as DRI-WEAVE by The Procter & Gamble Company on sanitary napkins.

The substrate 50 can be fibrous, and can be in the form of a woven or non-woven patch, batt, tow, tuft, or bundle of a fibers which are non-absorbent with respect to the volatile liquid substance. By "non-absorbent" it is meant that when the substrate 50 is immersed in the volatile liquid substance, the individual fibers absorb an amount of the volatile liquid substance less than their own weight (less than one gram of the volatile liquid substance absorbed by the fiber per gram of fiber weight). Accordingly, the volatile liquid substance is stored in the interstitial space between fibers or along the fibers' surfaces, rather than inside the fibers themselves, thereby enhancing release of the volatile liquid substance from the substrate 50.

In one embodiment, the substrate can comprise fibers formed from a polymer such as polyolefin. Suitable fibers include but not limited to polyethylene, polypropylene, and polyester fibers. The substrate 50 can be joined, directly or indirectly, to the barrier layer 30. In the embodiment shown in FIG. 1, the substrate 50 is secured directly to an inwardly facing surface of the barrier layer 30 by a layer of adhesive 35. Suitable adhesives 35 include Findley Adhesive #2120 or Findley H2031 Adhesive available from Findley Adhesives, Inc. of Elmgrove, Wis., and Century 5227 Adhesive available from Century International Adhesive and Coating Corp. of Columbus, Ohio.

Figure 4:
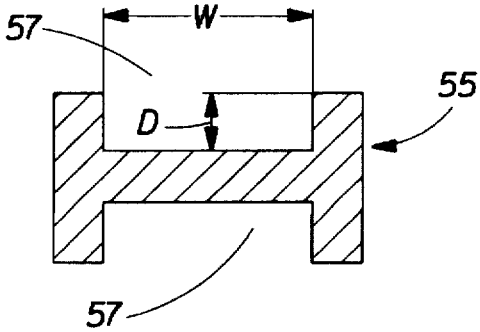
FIG. 4 is a a cross-sectional illustration of a capillary channel fiber having a generally I-shaped cross section.

In another embodiment, the substrate 50 can comprise a plurality of capillary channel fibers 55. Capillary channel fibers 55 are fibers that have one or more channels formed therein, preferably on their exterior surfaces. FIG. 4 shows a capillary channel fiber 55 having a generally I-shaped cross-section. It will be understood that suitable capillary channel fibers 55 can have any number of shapes, including but not limited to I, H, C, V, and U-shaped cross-sections. The channels 57 in the exterior surfaces of the fiber 55 can have a width W and a depth D. The value of W can be between about 10 microns and about 100 microns. The value of D can be between about 10 microns and about 100 microns. The capillary channel fibers 55 can have a denier of between about 10 and about 45 grams/9000 meters of fiber length. Suitable capillary channel fibers 55 are disclosed in the following references, which are incorporated herein by reference: U.S. Pat. No. 5,382,245 issued Jan. 17, 1995 to Thompson et al.; and U.S. Pat. No. 5,200,248 issued Apr. 6, 1993 to Thompson et al.

The value of W can be greater than or equal to the value of D. In on embodiment, the ratio of W/D can be at least about 1.5, and more preferably at least about 2.0. Such relatively shallow channels 57 having a relatively high W/D ratio are capable of transporting the volatile substance while providing for enhanced release of the substance from the substrate 50 compared to the release that would be provided with fibers 55 having channels 57 with lower W/D ratios. In one embodiment the value of D can be between about 15 microns and about 30 microns, and the value of W can be between about 40 microns and about 70 microns.

The substrate 50 can comprise a relatively high density region and a relatively low density region. The relatively high density region provides relatively rapid transport of the volatile fluid throughout the substrate, while the relatively lower density region promotes relatively rapid release of the volatile liquid material from the substrate. The fibers in at least a portion of the substrate 50 can be oriented in a predetermined direction, and in one embodiment the fibers in at least a portion of the substrate 50 are arranged in a generally parallel fashion to provide wicking of the volatile liquid in a predetermined direction.

Referring to FIG. 2, the substrate 50 can comprise a relatively low density region 54 extending between and joining two relatively high density regions 52A and 52B. The fibers in the relatively high density regions 52A and 52B can be arranged in a generally parallel fashion to provide wicking of the volatile liquid substance into the relatively low density region 54. The substrate shown in FIG. 2 can be formed from a length of generally parallel capillary channel fibers 55. The length of generally parallel capillary channel fibers can be compressed to buckle a portion of the fibers radially outwardly, thereby forming the relatively low density region 54.

In another embodiment, the substrate 50 can comprise a natural or synthetic sponge material, or an open celled foam material. Suitable open celled foams, such as foams prepared by polymerizing a high internal phase emulsion, are described in the following U.S. Patent documents, which are incorporated herein by reference: U.S. patent application Ser. No. 08/370,695, Absorbent Foams Made From High Internal Phase Emulsions Useful For Acquiring and Distributing Aqueous Fluids, filed Jan. 10, 1995 in the name of Stone, et al.; U.S. Patent Application entitled Absorbent Foams Made From High Internal Phase Emulsions Useful For Acquiring Aqueous Fluids, filed Aug. 30, 1995 in the name of DesMarais; U.S. Pat. No. 5,147,345; High Efficiency Absorbent Articles for Incontinence Management, issued Sep. 15, 1992 in the name of Young et al., which patent is incorporated herein by reference.

The material with which the substrate 50 is impregnated preferably comprises one or more components effective in repelling bugs, including but not limited to insects such as mosquitoes. In one embodiment, the substrate 50 can be impregnated with a liquid material comprising one or more organic compounds. Such organic compounds can have between one carbon atom and 20 carbon atoms (C1–C20 organic compounds), and more preferably, between 6 carbon atoms and 12 carbon atoms (C6–C12 organic compounds). In one embodiment, the substrate 50 is impregnated with a liquid material comprising one or more C6–C12 organic compounds. Such organic compounds can be saturated, unsaturated, or aromatic, and can have straight carbon chains, branched carbon chains, or cyclical structures.

Examples of suitable organic compounds include, but are not limited to, alcohols, such as cintronellol; aldhehydes, such as citronellal; ketones; esters; amids, and lactones. One suitable mixture with which the substrate 50 can be impregnated is CITRONELLA CEYLON, designated Flt FDG, FP 138, manufactured by International Flavors and Fragrances of New Jersey. Other suitable materials with which the substrate 50 can be impregnated include but are not limited to Ethyl Butylacetylaminopropinate; N,N diethyl-M-toluamide (DEET); and Dimethyl Phthalate.

The structures of the present invention can have a substrate 50 impregnated with an initial loading of about 2.0 grams or less of the volatile liquid material, and in one embodiment, with about 1.0 grams or less of the volatile liquid material. The ratio of the weight of the initial loading of the volatile liquid material to the weight of the dry substrate should be at least about 0.1. In one embodiment, the ratio of the weight of the initial loading of the volatile liquid material to the weight of the dry substrate 50 is preferably at least about 2.0, and in one embodiment at least about 4.0. By way of illustrative example, the substrate 50 can have a dry weight of about 0.22 grams impregnated with about 2.0 grams of a liquid comprising citronella oil, such as the above referenced CITRONELLA CEYLON.

The structures of the present invention can provide an effective release rate of insect repellent material with a relatively small amount of insect repellent material. Without being limited by theory, it is believed that the ability of the structures of the present invention to provide an effective release rate with a small amount of insect repellent is due, at least in part, to having a relatively high ratio of weight of the initial loading of insect repellent material to dry substrate weight.

In the embodiment shown in FIG. 1, the substrate 50 can be impregnated with the volatile liquid material, and then sealed in the wrapper 22. In an alternative embodiment shown in FIG. 5, the article 20 can comprise a liquid impermeable breakable vessel 90 containing a predetermined quantity of the volatile liquid 100, and a substrate 50 for receiving the predetermined quantity of volatile liquid 100. The breakable vessel 90 is breakable by a user to direct the volatile liquid 100 to the substrate 50. The breakable vessel maintains the volatile liquid material separate from the substrate 50 until the article 20 is ready to be used. Accordingly, the volatile liquid substance is less likely to evaporate from the article 20 prior to the time the article is placed in use.

The breakable vessel 90 can comprise a packet formed from a liquid impervious layer of material. For instance, the vessel 90 can comprise a packet formed from a polymeric film, such as a thermoplastic film. Such a packet can also be formed from a laminate of foil and a polymeric film. Suitable materials from which the vessel 90 can be formed include the films and laminate from which the barrier layer 30 can be formed, as described above. In one embodiment, the vessel 90 can be formed from a film manufactured by Tredegar Industries of Terre Haute, Ind. under the designation C-8570 and having a thickness of about 0.028 mm.

Figure 5:
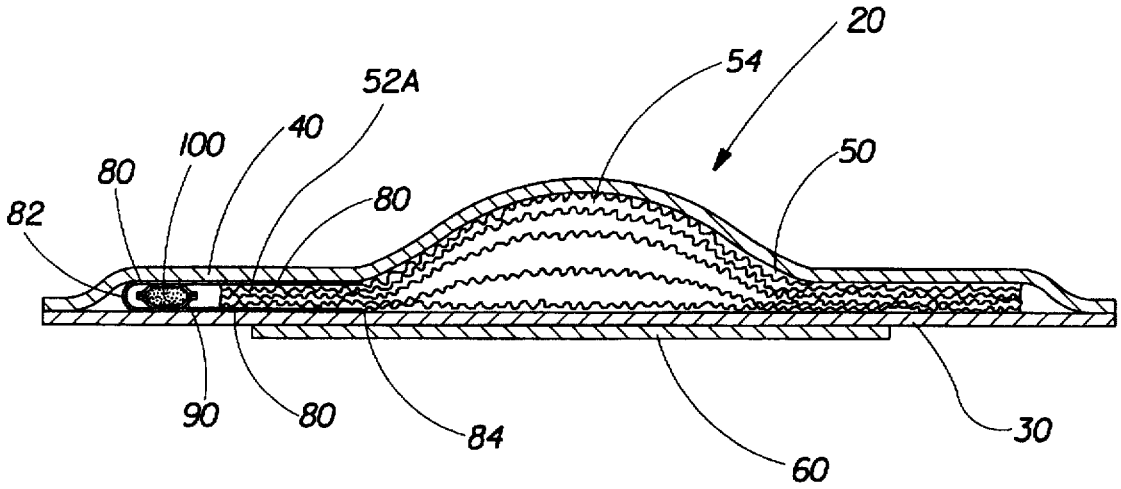
FIG. 5 is a cross-sectional view of an alternative embodiment of the present invention having a breakable vessel containing the volatile liquid insect repellent positioned intermediate the porous cover layer and the barrier layer.

The breakable vessel 90 and at least a portion of the substrate 50 can be disposed in a fluid conduit. The fluid conduit directs the predetermined amount of volatile liquid 100 from the vessel 90 to the substrate 50, once the vessel 90 is broken. In FIG. 5, the fluid conduit comprises a sleeve 80 having a closed end 82 and an open end 84. The vessel 90 is disposed in the sleeve 80 adjacent the closed end 82. At least a portion of the relatively high density region 52A of the substrate 50 extends into the open end 84 of the sleeve 80. Generally parallel capillary channel fibers 55 in the region 52A extend into the sleeve 80 to wick fluid from the broken vessel 90 to the relatively low density region 54.

The sleeve 80 can be joined to the substrate 50 to form a fluid seal. For instance, the open end 84 of the sleeve 80 can be adhesively joined to the substrate 50 to prevent the predetermined amount of liquid 100 from flowing between the substrate 50 and the sleeve 80. The sleeve can be formed of a liquid impermeable film, such as a polymeric film which is substantially non-absorbent with respect to the volatile liquid substance. Suitable materials from which the sleeve can be formed include those films and laminate from which the barrier layer 30 can be formed. Another suitable film from which the sleeve 80 can be formed is SARAN brand wrap manufactured by Dow Brands, Inc. of Indianapolis, Ind.

Figure 6:
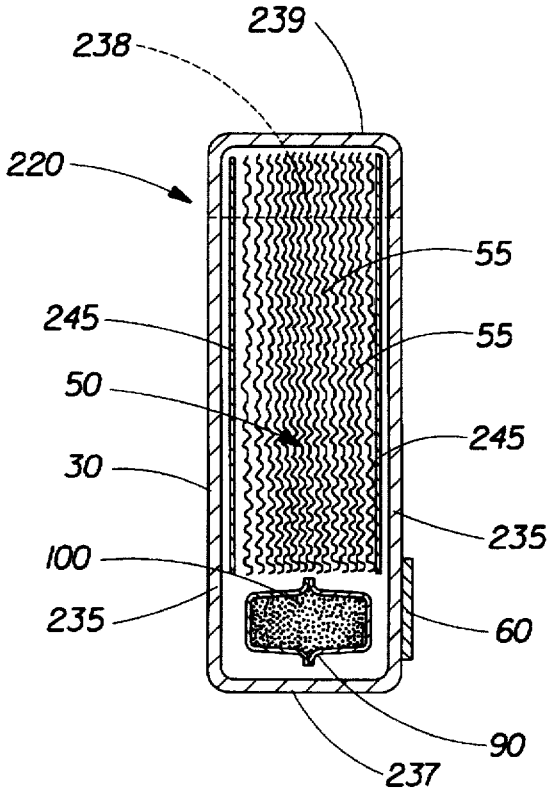
FIG. 6 is a cross-sectional view of an alternative embodiment of the present invention having a substrate formed of generally parallel capillary fibers and a breakable packet of the volatile liquid disposed in an elongated package having a removable end.

FIG. 6 is a cross-sectional view of an alternative embodiment of the present invention. In FIG. 6, an article 220 according to the present invention comprises a substrate 50 formed of generally parallel capillary fibers 55 and a breakable vessel 90 containing a predetermined amount of a volatile liquid 100. The substrate 50 and the breakable vessel 90 are disposed in an elongated package 235. A fastener 60 can be disposed on an external surface of the package 235.

The package 235 can have a generally cylindrical shape, and can have a first end 237 and a second removable end 239. The second removable end 239 can be separated from the package 235 at a line of weakness, such as along a line of perforations 238. The package 235 preferably comprises a liquid impermeable film, such as a plastic film which is substantially non-absorbent with respect to the volatile liquid substance. Suitable materials from which the package 235 can be formed include those films and laminate from which the barrier layer 30 can be formed.

The breakable vessel 90 can be disposed in the package 235 adjacent the first end 237. The fibers 55 can extend in a generally parallel fashion from the vessel 90 to the second end 239. The fibers 55 can be transversely restrained by a sheath 245. The sheath 245 can comprise one or more layers of paper which encircle the fibers 55 and maintain the fibers 55 in a radially compact, generally cylindrical form. Orienting the fibers 55 in a general parallel fashion, and maintaining the fibers 55 in a radially compact form along at least a portion of their lengths is desirable. Such a fiber configuration is desirable for wicking the volatile liquid material from the vessel 90 toward the second end 239.

Figure 7:
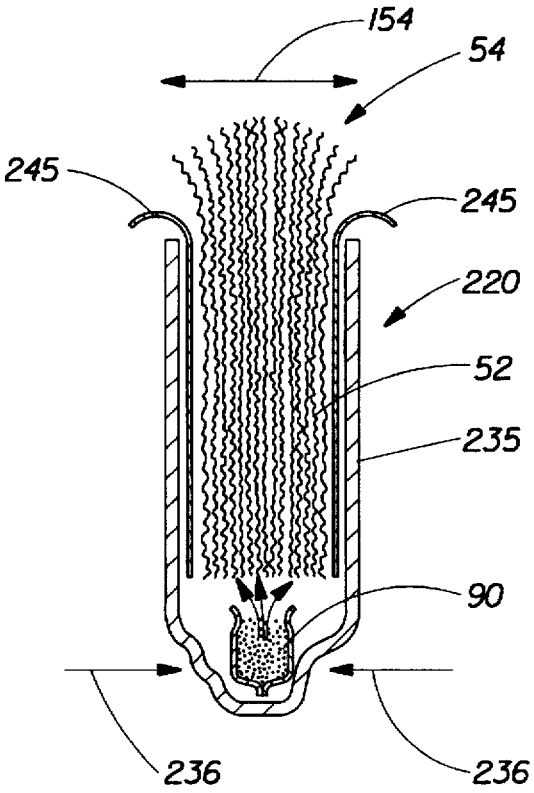
FIG. 7 is a cross-sectional view of the article of FIG. 6 showing the end of the elongated package removed to provide a relatively low density portion of the substrate extending from the package.

FIG. 7 is a cross-sectional view of the article 220 of FIG. 6 showing the removable end 239 detached from the elongated package 235. With the removable end 239 detached from the package, a portion of the sheath 245 adjacent to the end 239 can be peeled back to free the ends of the fibers 55, as shown in FIG. 7. Freeing the ends of the fibers 55 permits the ends of the fibers to expand transversely as indicated by the arrows 154 in FIG. 7, such as in a radial direction, thereby forming a a relatively low density region 54 of the substrate 50. The portion of the substrate 50 which remains encircled by the sheath 245 comprises a relatively high density region 52. The vessel 90 can be broken by exerting oppositely directed compressive forces on either side of the package 235 (e.g. by pinching the package 235 between two fingers) as indicated by arrows 236.

Figure 8:
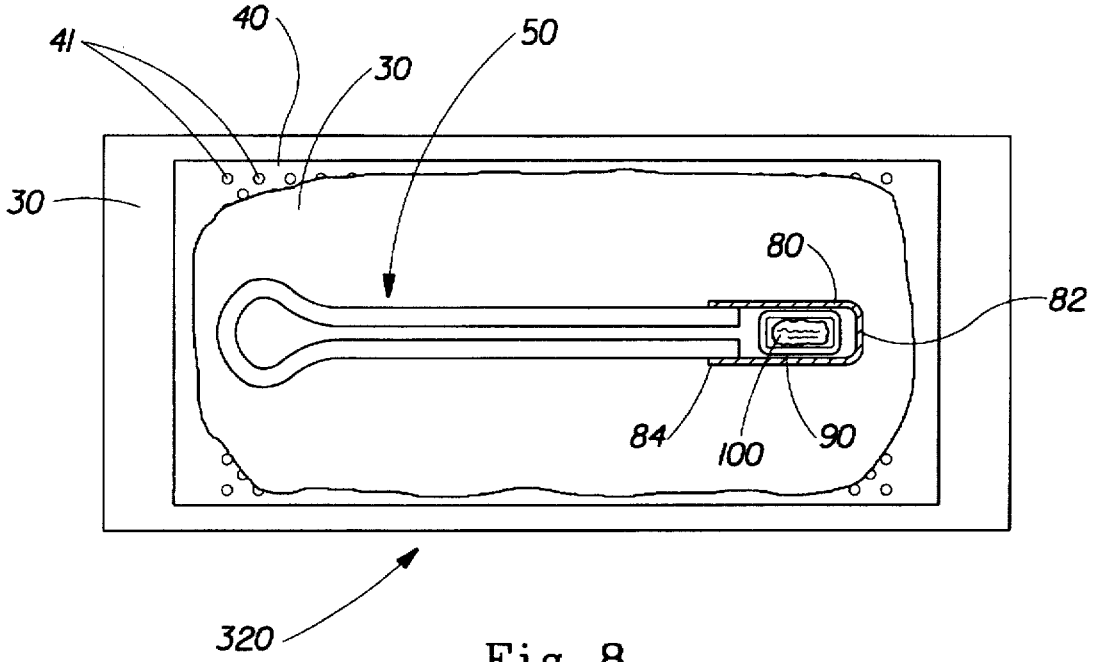
FIG. 8 is an alternative embodiment of the present invention having a substrate formed of a strand of woven polyolefinic fibers and a breakable vessel connected to the substrate through a fluid conduit.

FIG. 8 is a partially cut away top plan view of an article 320 according to an alternative embodiment of the present invention. The article 320 comprises a barrier layer 30, a porous cover layer 40 joined to the barrier layer 30, and a substrate 50 disposed intermediate the barrier layer and the porous cover layer 40. The substrate 50 comprises a strand of braided polyolefinic fibers. The strand of braided fibers can have two ends disposed in a sleeve 80, to be positioned adjacent a breakable vessel 90 containing the volatile liquid substance. In yet another embodiment, the substrate 50 can comprise a woven or non-woven web of non-absorbent fibers in the form of a patch. Such a patch can comprise polypropylene fibers, and can have a basis weight of about 5–6 ounces per square yard and a caliper of between about 0.05 inch and about 0.10 inch.

In another embodiment, the substrate 50 can comprise a nonwoven web of paper fibers, including paper webs manufacture by through air drying techniques as well as by conventional papermaking techniques. Suitable webs from which the substrate 50 can be formed are disclosed in the following U.S. Patents, which are incorporated herein by reference: U.S. Pat. No. 4,528,239 issued Jul. 9, 1985 to Trokhan; U.S. Pat. No. 5,277,761 issued Jan. 11, 1994 to Phan et al.; and U.S. Pat. No. 5,245,025 issued Sep. 4, 1993 to Trokhan et al. In one embodiment, the substrate 50 can have a weight of about 0.25 grams, and can comprise 2 or more sections of 2-ply paper towels cut from BOUNTY brand paper towels manufactured by The Procter and Gamble Company.

Figure 9:
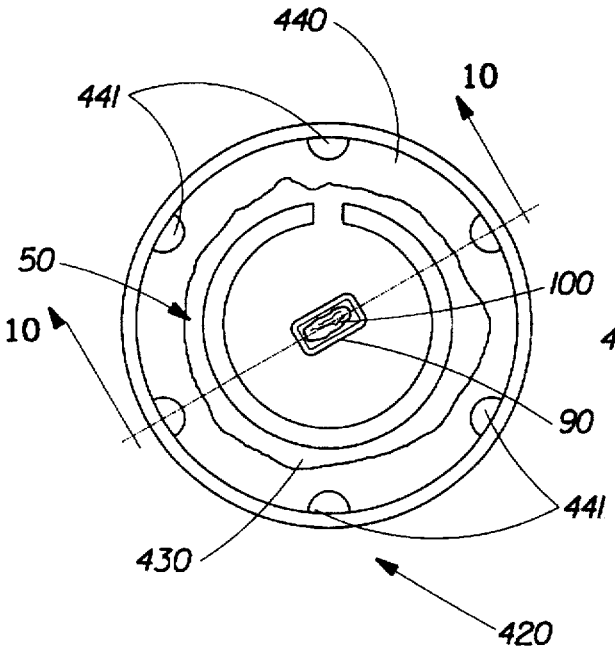
FIG. 9 is a top plan view of an alternative embodiment of the present invention having the substrate and the breakable vessel enclosed in a container, with a portion of the top surface of the container shown cut away.
Figure 10:
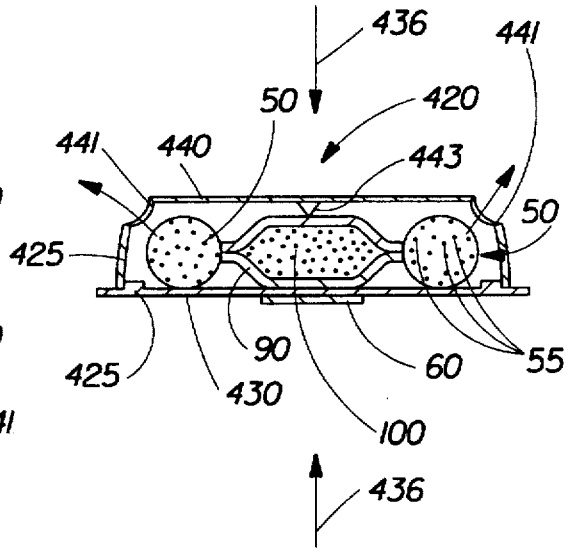
FIG. 10 is a cross-sectional view of the article shown in FIG. 9 taken along the lines 10—10.

FIGS. 9 and 10 show an article 420 according to an alternative embodiment of the present invention. The article 420 comprises a container 425. The container 425 can comprise a shell 440 having apertures 441 therethrough. The shell 440 can be joined directly or indirectly to a base 430, such as by adhesive, by interference fit, or by other suitable means. A fibrous substrate 50 and a breakable vessel 90 containing a predetermined amount of volatile liquid 100 are shown disposed in the container, intermediate the shell 440 and the base 430. The shell 440 and the base 430 can be thermoformed from thermoplastics.

A piercing element 443 can be joined to or extend integrally from an inside surface of the shell 440. The breakable vessel 90 can be positioned subjacent the piercing element 443. The substrate 50 can at least partially encircle the vessel 90, so that fibers 55 of the substrate 50 extend around the vessel 90 in a generally parallel fashion.

The shell 440 can be resiliently or plastically deformed relative to the base 430, such as by applying oppositely directed compressive forces 436 to the shell and base (e.g. by squeezing the shell and base between two fingers). Deflection of the shell relative to the base causes the piercing element 443 to pierce the vessel 90, thereby releasing the volatile liquid to impregnate the substrate 50. Vapors of the volatile liquid substance are then released through the apertures 441 in the shell 440.

RELEASE RATE MEASUREMENT

The release rate of an article having volatile liquid material is measured using the following procedure. The release rate is measured in a KEM PONENT brand fume hood chamber with the vent closed and the fan turned off, and the chamber measuring approximately 4 foot by 3 foot by 4 foot. The chamber is maintained at a temperature of about 70 degrees. The pressure in the chamber is maintained at about 1 atmosphere and the relative humidity in the chamber is maintained at about 55 percent. A ring stand is positioned in the chamber to support articles for which the release rate is to be measured.

For articles having a substrate pre-impregnated with a volatile liquid material and sealed to prevent evaporation of the volatile liquid material, the release rate is determined using the following measurements. The seal preventing evaporation is removed, and the article is immediately weighed on a balance located in the chamber to obtain a beginning article weight, or WB, in grams. The article is then supported on the ring stand in the chamber. After one hour, the article is again weighed on the balance. This weight is the one-hour article weight, W1. The article weight is re-measured at one-hour intervals to obtain the two-hour article weight, W2; the three-hour article weight, W3; and the four hour article weight, W4. The article is supported on the ring stand in the chamber between each weight measurement.

After four hours, the article is supported on the ring stand and periodically reweighed until substantially all the volatile material has escaped from the article, such that there is no significant change in the weight of the article on subsequent re-weighings at one hour intervals. The weight of the article at this point is the dry article weight, WD.

The macroscopic surface area of the substrate 50 which was wetted by the volatile liquid material is designated SA, and is measured in square inches. By macroscopic surface area, it is meant the surface area of the substrate calculated from the perimetric dimensions (e.g. width and length) of the substrate, as differentiated from the micro-surface area of individual fibers or filaments making up the substrate. The surface area SA is measured when the substrate is substantially dry.

Those portions of the surface area of the substrate which are sealed (such as by a sleeve 80) so that they cannot release the volatile liquid material are not counted in the area measurement SA. If the article being measured has a porous cover layer 40, the surface area SA is the portion of the surface area of the substrate which underlies the porous cover layer 40 and which is capable of releasing the volatile liquid material (i.e. not sealed, such as by a sleeve 80). By way of example, the surface area SA of the substrate 50 shown in FIGS. 1–2 would be the combined surface areas of the regions 52A, 52B, and 54 underlying the porous cover 40, as viewed in FIG. 2. In the embodiment shown in FIG. 5, the surface area SA would not include the portion of region 52A covered by sleeve 80. In the embodiment of FIGS. 6 and 7, the surface area SA is the surface area of the generally cylindrical portion of the substrate 50 extending outward from the sheath 245. In an alternative embodiment, the generally cylindrical substrate 50 in FIGS. 6 and 7 can be sealed except at one end (e.g. the sheath 245 extends along the entire length of the substrate 50, and is not peeled back, so that material is released only from the ends of the fibers 55.) In that case, the surface area SA would be the area of the circular shaped cross-section of the substrate 50.

For articles having a substrate which is not pre-impregnated with a volatile liquid material, the release rate is determined from the following measurements. The macroscopic surface area, SA, of the dry substrate is measured. The dry article weight, WD, is measured with a balance. The article is then impregnated with the volatile liquid material, and immediately weighed with a balance to obtain the beginning article weight, WB. The article is then supported on the ring stand in the chamber. After one hour, the article is again weighed on the balance. This weight is the one-hour article weight, W1. The article weight is re-measured at one-hour intervals to obtain the two-hour article weight, W2; the three-hour article weight, W3; and the four hour article weight, W4. The article is supported on the ring stand in the chamber between each weight measurement.

The release rate of articles having preimpregnated and non-preimpregnated substrates can be calculated as follows. The weight of the volatile liquid material initially on the article is WL and is equal to WB-WD, in grams. The one-hour release rate of the article is the weight, in grams, of volatile liquid material released in the first hour, per square inch of surface area SA of the substrate, per gram of volatile liquid material initially on the article. The one-hour release rate R1 is calculated as:

$$(WB\text{-}W1 \text{ grams/hour})/[(WL \text{ grams})\times(SA \text{ square inches})]$$

The two hour release rate, R2, can be calculated as follows:

$$(W1\text{-}W2 \text{ grams/hour})/[(WL \text{ grams})\times(SA \text{ square inches})]$$

The three hour release rate, R3, can be calculated as follows:

$$(W2\text{-}W3 \text{ grams/hour})/[(WL \text{ grams})\times(SA \text{ square inches})]$$

The extended four hour release rate, R4, can be calculated as follows:

$$(W3\text{-}W4 \text{ grams/hour})/[(WL \text{ grams})\times(SA \text{ square inches})]$$

In at least one embodiment, the present invention provides an extended four hour release rate R4 which is at least about 50 percent, and more preferably at least about 80 percent of the one-hour release rate R1.

EXAMPLES OF MEASURED RELEASE RATES

Table 1 provides the number of grams of liquid material released from seven articles having different substrate materials. The articles 1–5 each comprised a barrier layer formed from the above referenced M2077 foil/film laminate and a porous cover formed from porous tape manufactured by The 3M Company under the brand name Transpor and having an open area ratio of about 10 percent.

The substrate of article 1 comprised about 0.45 grams dry weight of BOUNTY brand paper toweling. The substrate of article 2 comprised about 0.45 gram of a wood pulp material taken from a BANDAID brand bandage manufactured by Johnson and Johnson of Skillman, N.J. The substrate of article 3 comprised about 0.69 grams of a web of polypropylene fibers taken from an Adhesive Pads manufactured by Johnson and Johnson. The substrate of article 4 comprised about 0.22 grams of an open celled foam material manufactured according to the teachings of U.S. patent application Ser. No. 08/370,695, Absorbent Foams Made From High Internal Phase Emulsions Useful For Acquiring and Distributing Aqueous Fluids, filed Jan. 10, 1995 in the name of Stone, et al. The substrate of article 5 comprised about 0.65 grams of a synthetic sponge material manufactured by The 3M Company under the tradename O-CEL-O.

Article 6 comprised a generally cylindrical bundle of generally parallel polyethylene capillary channel fibers. The substrate comprised about 0.38 grams of capillary channel fibers having an I-shaped cross-section having a channel width W of about 60 microns and a channel depth D of about 24 microns, the fibers in the form of a tow manufactured by Eastman Chemical Co. of Kingsport, Tenn. under the designation SW-361 Tow @ 40M Total Denier. The bundle of fibers was enclosed in a plastic film with only one, generally circular shaped end of the fiber bundle exposed. Accordingly, the volatile material added to the bundle of fibers was only released from the one exposed, generally circular shaped end of the bundle of fibers. The surface area SA of such a substrate is the area of the exposed, circular shaped end of the fiber bundle.

Article 7 comprised a barrier layer formed from the above referenced M2077 foil/film laminate, a porous cover comprising an apertured formed plastic film having an open area ratio of between about 30–40 percent, apertures having a surface area of between about 0.35–0.45 square millimeter, and a caliper of between about 0.018–0.025 inch. The substrate comprised about 0.94 grams of capillary channel fibers having an I-shaped cross-section having a channel width W of about 60 microns and a channel depth D of about 24 microns, the fibers in the form of a tow manufactured by Eastman Chemical Co. of Kingsport, Tenn. under the designation SW-361 Tow @ 40M Total Denier. The substrate had two relatively high density ends wrapped in SARAN brand wrap, and a middle relatively low density portion having a macroscopic surface area SA of about 0.75 square inches.

The substrates of each of the article 1–7 were impregnated with the above referenced CITRONELLA CEYLON. Table 1 includes the macroscopic surface area SA of each substrate, the amount of CITRONELLA CEYLON added to the substrates, and the amount of the liquid released by the articles at one, two, three, and four hour intervals. Table 2 provides the one, two, three, and four-hour release rates for each of the six articles.

One and two-hour release rates were also measured for a first sample of a commercially available bug repellent patch marketed as REPELLO-PATCH by P.J. Maxwell. The sample REPELLO-PATCH tested had a dry, uncovered substrate having a surface area SA of about 3.5 square inches and a separately packaged liquid material which was added to the substrate. The substrate weighed about 0.59 grams, and included synthetic polymeric fibers and an adhesive backing. The separately packaged liquid material was labeled as being 99 percent citronella. About 0.75 grams of the separately packaged liquid material was added to the substrate. The one hour release rate was determined to be about 0.0098 grams/square inch-gram-hour, and the two hour release rate was determined to be about 0.0074 grams /square inch-gram-hour. One, two, three, and four-hour release rates for a second sample of a REPELLO-PATCH brand path were also measured, with the following results in grams/square inch-gram-hour: 0.0048, 0.0040, 0.0036, and 0.0034.

TABLE 1

| | | SA | Load | Release Amounts (grams) | | | |
|---|---|---|---|---|---|---|---|
| Art. | Substrate | (sq. in.) | (grams) | 1 Hr | 2 Hr | 3 Hr | 4 Hr |
| 1 | Wood Pulp 1 | 6.00 | 2.0 | 0.108 | 0.105 | 0.101 | 0.107 |
| 2 | Wood Pulp 2 | 6.00 | 3.0 | 0.177 | 0.181 | 0.199 | 0.214 |
| 3 | Poly Prop Fiber | 3.00 | 1.5 | 0.075 | 0.071 | 0.056 | 0.035 |
| 4 | Foam | 2.25 | 2.0 | 0.129 | 0.122 | 0.110 | 0.086 |
| 5 | Sponge | 2.25 | 2.0 | 0.171 | 0.155 | 0.074 | 0.089 |
| 6 | Capillary Channel Fiber | 0.07 | 1.0 | 0.015 | 0.013 | 0.015 | 0.013 |
| 7 | Capillary Channel Fiber | 0.75 | 2.0 | 0.087 | 0.052 | 0.053 | 0.058 |

TABLE 2

| Art. | Substrate | SA (sq. in.) | Load (grams) | Release Rates (grams/sq in-gm-hr) 1 Hr | 2 Hr | 3 Hr | 4 Hr |
|---|---|---|---|---|---|---|---|
| 1 | Wood Pulp 1 | 6.00 | 2.0 | 0.009 | 0.009 | 0.008 | 0.009 |
| 2 | Wood Pulp 2 | 6.00 | 3.0 | 0.010 | 0.010 | 0.011 | 0.012 |
| 3 | Poly Prop Fiber | 3.00 | 1.5 | 0.017 | 0.013 | 0.013 | 0.008 |
| 4 | Foam | 2.25 | 2.0 | 0.028 | 0.027 | 0.024 | 0.019 |
| 5 | Sponge | 2.25 | 2.0 | 0.038 | 0.026 | 0.016 | 0.019 |
| 6 | Capillary Channel Fiber | 0.07 | 1.0 | 0.210 | 0.181 | 0.201 | 0.216 |
| 7. | Capillary Channel Fiber | 0.75 | 2.0 | 0.058 | 0.034 | 0.035 | 0.039 |

In the embodiments described, the substrate 50 is impregnated with substance effective for repelling insects. In other embodiment, the substrate 50 can be impregnated with materials which are effective in providing a desired fragrance, such as perfume materials, or combinations of such materials.

While particular embodiments of the present invention have been illustrated and described, it would be obvious to those skilled in the art that various changes and modifications can be made without departing from the spirit and scope of the invention. It is intended to cover, in the appended claims, all such modifications and intended uses.

What is claimed is:

1. A portable disposable article for providing controlled release of a volatile liquid material, the article having a release rate of at least about 0.015 grams/gram-square inch-hour of the volatile material.

* * * * *